US00PP12414P2

(12) United States Plant Patent
Chang

(10) Patent No.: US PP12,414 P2
(45) Date of Patent: Feb. 19, 2002

(54) STRAWBERRY PLANT CALLED 'TREASURE'

(76) Inventor: Peggy Pai-Chi Chang, 5983 Green Blvd., Naples, FL (US) 34116

( * ) Notice: Subject to any disclaimer, the term of this patent is extended or adjusted under 35 U.S.C. 154(b) by 0 days.

(21) Appl. No.: 09/497,675

(22) Filed: Feb. 4, 2000

(51) Int. Cl.[7] ..... A01H 5/00
(52) U.S. Cl. ..... Plt./208
(58) Field of Search ..... Plt./208, 209

*Primary Examiner*—Bruce R. Campell
*Assistant Examiner*—Susan B. McCormick

(57) ABSTRACT

'Treasure' is a new and distinct short-day cultivar of strawberry plant, which produces sweet and firm fruits. Compared to 'Camarosa', 'Treasure' produces more consistent conic fruit shape and the color is more dark red. It produces higher yields and larger quantities of early-season fruits than 'Camarosa' when grown in central and south Florida. Fruiting plant size of 'Treasure' is smaller and more compact than 'Camarosa'.

3 Drawing Sheets

BACKGROUND OF THE INVENTION

The invention of 'Treasure', a new and distinctive cultivar of strawberry plant, is a result of the cross breeding between 'A3' (an unpatented J&P selection) and 'Oso Grande' (U.S. Plant Pat. No. 6,578). The resulting plant was selected in a controlled breeding plot at J&P Research's cultivated field located in Naples, Fla. during the fruiting season of 1997–1998. It was designated as JP3 by the inventor. This cultivar is botanically identified as *Fragaria xananassa Duch*. 'Treasure' has been propagated by runner and meristem culture in Naples, Fla. as well as in the commercial nurseries in United States and Canada. It has been trialed in the fields of growers in both North Carolina and Florida. A 'Treasure' plant retains its distinctive characteristics and reproduces true to type in successive generations.

COMPARISON TO CLOSEST CULTIVARS

The commerical cultivar that we believe to be the closest comparison to 'Treasure' in appearance from those known to us is 'Camarosa'(U.S. Plant Pat. No. 8,708).

However, there are several characteristics of 'Treasure' that are different from or not possessed by 'Camarosa'. Those are:

(1). Color: The fruit color of 'Treasure' is dark red, which is very distinguishable when compared with 'Camarosa'.

(2). Productivity: 'Treasure' is a much earlier producer and has a higher total yield in comparison to 'Camarosa' in Florida production areas.

(3). Plant size: The plant size of 'Treasure' is much smaller than that of 'Camarosa'.

(4). Anthracnose crown rot resistance: The plant of 'Treasure' is tolerant to anthracnose crown rot disease, which is one of the major diseases in strawberry growth in the southeastern United States, and 'Camarosa' is susceptible to anthracnose disease.

(5). Bracts: The frequency of bracts, which occur on the petioles of 'Treasure' is 63.6% , wherease there are none on 'Camarosa'.

(6). Isozymes in leaf extracts: For isozyme analyses see Table 1.

(a) The phosphoglucoisomerase (PGI) isozyme banding pattern for 'Treasure' and 'Camarosa' is A2.
(b) The leucine aminopeptidase (LAP) isozyme banding pattern for 'Teasure' and 'Camarosa' is B3.
(c) The malate dehydrogenase(MDH) isozyme banding pattern for 'Treasure' is C1 whereas 'Camarosa' is C2.

All isozyme analyses were conducted using leaf tissue. Reference: J. Amer. Soc. Hort. Sci. 106:684–687,(1981); USDA Forest Service General Technical Report PSW-64, (1982); and Tanksley, S. D. and Orton, T. J. Isozymes in Plant Genetics and Breeding, Part A, pp. 469–516 (Elsevier Science Publishers B.V., 1984).

TABLE 1

Isozyme in leaf extracts by electrophoresis

| | Treasure | Camarosa |
|---|---|---|
| PGI | A2 | A2 |
| LAP | B3 | B3 |
| MDH | C1 | C2 |

As shown in Table 1 'Treasure' can be unambiguously distinguished from 'Camarosa' by using the above-mentioned isozyme patterns.

DESCRIPTION OF THE NEW CULTIVAR

Figure 1:
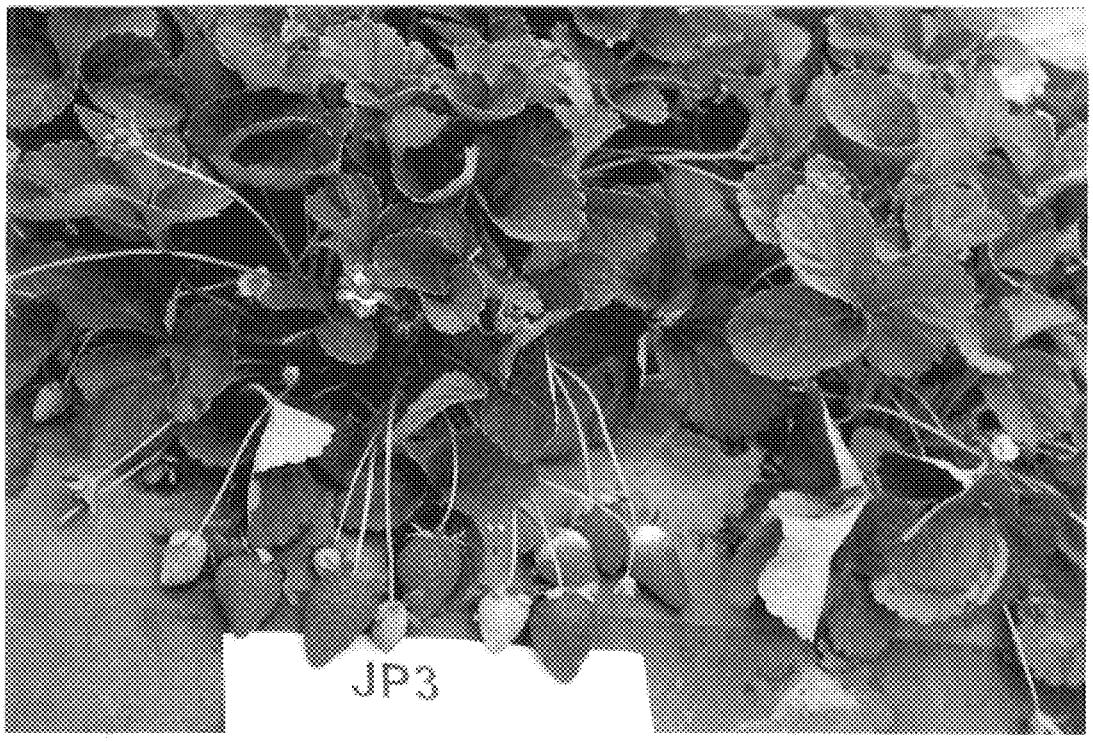
FIG. 1 shows the general flowering and fruiting characteristics of the plants during mid-season fruit production in Florida.
Figure 2:
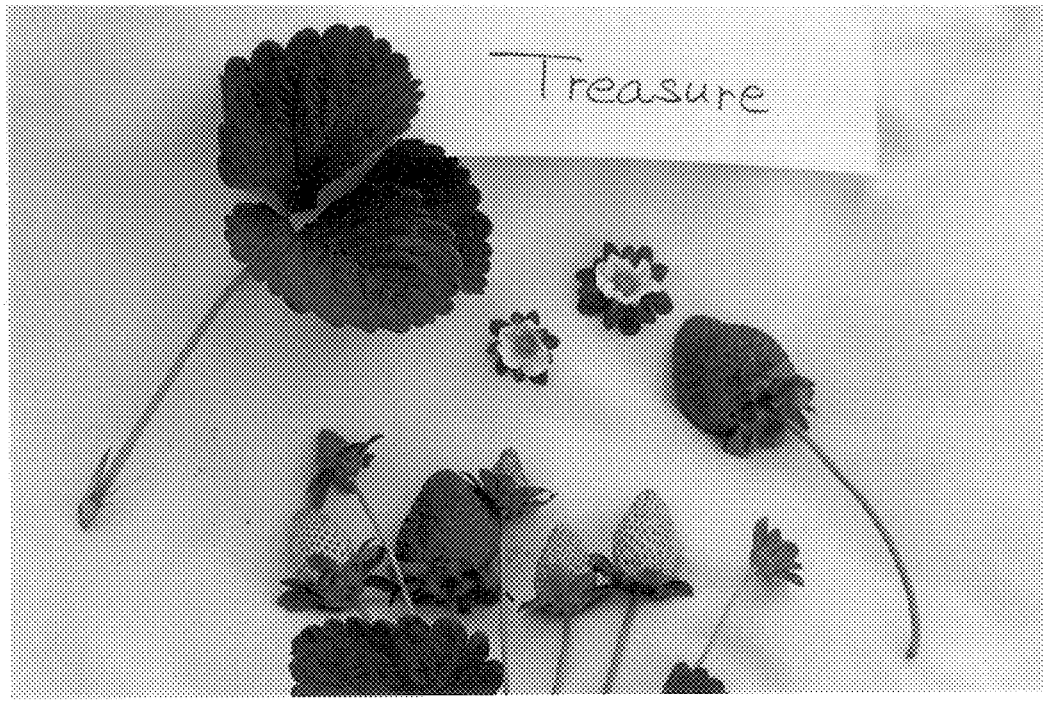
FIG. 2 depicts a) a typical mature compound leaf, b) a representative complete flower during the mid-fruiting season, c) a partial fruiting truss including different stages of flowering and fruiting, and d) a typical mature fruit.
Figure 3:
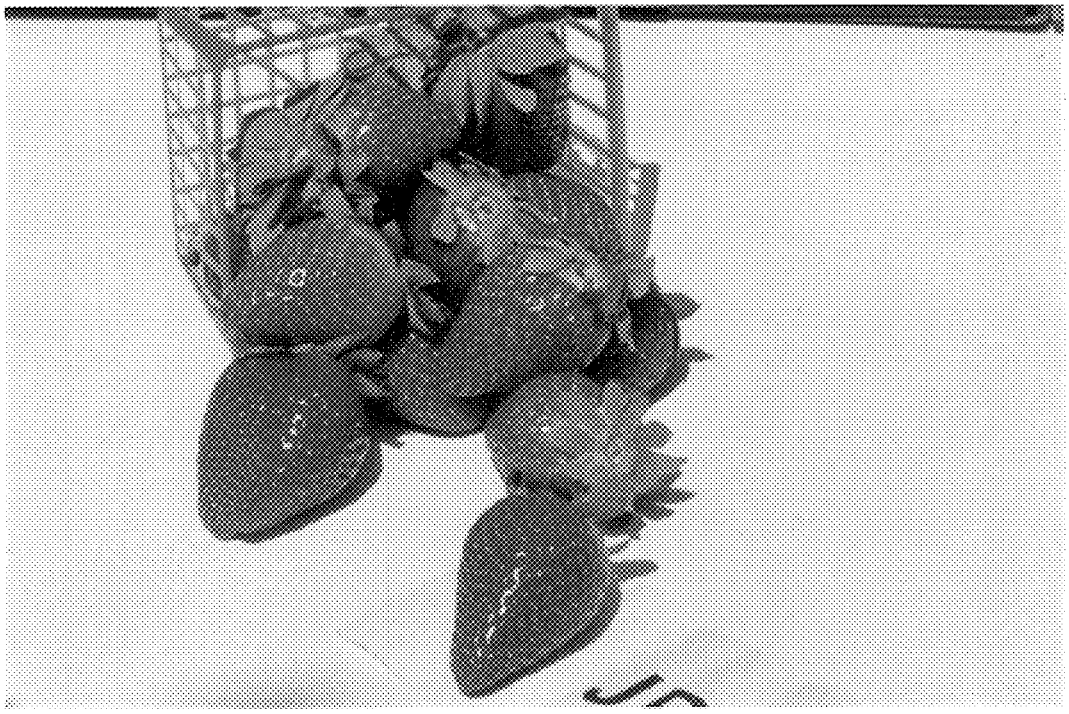
FIG. 3 shows plural fruit of the claimed plant reflecting the variation in fruit shape and size within market grade and shows seed and calyx placement relative to the fruit surface, as well as the attractive and uniform coloration of the ripe fruit at harvest stage.

'Treasure' is a new and distinctive short-day type strawberry cultivar which is the result of a cross breeding between J&P selection 'A3' (an unpatented J&P selection) and 'Oso Grande'. The female parent 'A3' possesses the distinguishable characteristics of very large fruit size, good yield, superior conic shape, glossy color, rich flavor and anthracnose crown rot resistance. The male parent 'Oso Grande' possesses the distinguishing characteristics of large fruit size, good firmness and very good flavor. The novel cultivar 'Treasure' resembles the female parent in possessing the characteristics of large fruit size, superior shape, good flavor, anthracnose crown rot resistance and resembles the male parent in possessing the characteristics of firm fruit and good flavor. 'Treasure' is superior to both parents with respect to the characteristics of a more vigorous plant, earlier production, higher yield, firmer fruit ,much sweeter flavor and longer shelf life.

'Treasure' is an early fruiting cultivar, which has performed well in trials in Florida during the 1998–99 fruiting season. It is competive with 'Camarosa' and 'Sweet Charlie' (U.S. Plant Pat. No. 8,729) the two most important cultivars grown in Florida at this time. 'Treasure' fruits earlier than 'Camarosa', but a little later than 'Sweet Charlie'. Yield of 'Treasure' is higher than those from 'Camarosa' and 'Sweet Charlie'.

The distinctive characteristics of this new strawberry cultivar, described in detail below were observed upon its discovery and throughout the repeated test periods.

PLANTS AND FOLIAGE

The plants and foliage characteristics of 'Treasure' were collected about 4 month after planting the plants in fruiting field are listed in Table 2.

Table 2

Plant & Foliage characteristics for 'Treasure'

Plant

Average size:
- *Height* (*mm*).—192.
- *Diameter* (*mm*).—370.

Shape: Globose.
Density: Medium to open.
Vigor: Strong.
Root initiation: Slow rooting, about 5 days to 3 weeks.

Foliage

Terminal leaflet:
- *Length* (*mm*).—62.
- *Width* (*mm*).—61.

Shape of terminal leaflet: Orbicular with serrulate margin.
Color (Munsell color charts):
- *Abaxial*.—5GY 3/4.
- *Adaxial*.—5GY 5/4.

Leaf pubescence: Moderate and direction is acropetal.
Serrations number of terminal leaflets (mean): 19.
Petiole:
- *Length* (*mm*).—203.
- *Diameter* (*mm*).—3.
- *Color* (*Munsell color charts*).—5GY 7/6.
- *Pubescence*.—Heavy and direction is acropetal.

Petiolule:
- *Length* (*mm*).—11.
- *Diameter* (*mm*).—1.5.
- *Color* (*Munsell color charts*).—5GY 6/6.

Base angles of terminal leaflets(half blade) (degree): 63.
Bract leaflet position(distance from base to bract/petiole length): 0.75.
Stolons:
- *Number*.—Many.
- *Anthocyanin coloration*.—High.
- *Thickness* (*diameter, mm*).—2.
- *Pubescence*.—Moderate and direction is acropetal.

RESISTANCE TO DISEASE AND STRESS

'Treasure' has relatively high tolerance to anthracnose crown rot, which is similar to 'Sweet Charlie', but better than 'Camarosa'. 'Treasure' is relatively tolerant to Botrytis when compared to 'Sweet Charlie' and 'Camarosa'. 'Treasure' is moderately tolerant to rain cracking and high and low temperatures. It generally does not have exposure to drought under our growing condition.

FLOWERING AND FRUITING CHARACTERISTICS

The distinguishing flowering and fruiting characteristics of 'Treasure' plants were collected about 4–5 month after planting the plants are presented in Table 3. The flowers are self-fertile and pollination is excellent. The center of the fruit is solid with little to no hollowing. The Canadian-produced 'Treasure' plants typically begin to harvest about seven weeks after planting in Florida commercial production area.

Table 3

Flower and fruit characters for 'Treasure'.

Bud: At the stage of largest size, 1 day before flower opens.
- *Diameter* (*mm*).—24.
- *Length* (*mm*).—17.
- *Color* (*Munsell color charts*).—Upper: 5GY 6/10. Base: 5GY 6/4.

Flower: At fully open stage, 1 day after starting to open.
- *Diameter* (*mm*).—40.
- *Height* (*mm*).—93–125.
- *Number of flower/cluster*.—2–4.
- *Fragrance*.—None.

Bloom time and period in specific location: Observed at the research plots of J&P Research Inc. In Naples, Fla.
Approximate of bud burst, bloom time & duration: The earliest buds open on plants planted mid-October Started 3 weeks after the plants were planted. Plants bloom from November until May.
Petals:
- *Length* (*mm*).—12.
- *Width* (*mm*).—12.
- *Shape*.—Obtuse. Apex: Obtuse. Base: Obtuse.
- *Color* (*no color chart given*).—White.
- *Texture*.—Smooth.
- *Margin*.—Entire.
- *Number*.—Mean: About 7. Range: 6–9.

Sepals:
- *Length* (*mm*).—15 .
- *Width* (*mm*) .—6.5.
- *Shape*.—Oblanceolate. Apex: Acute. Base: Cuneate.

*Color* (*Munsell color charts*).—Abaxial: 5GY4/6. Adaxial: 5GY 6/4.

*Number.*—Mean: 14. Range: 10–18.

Reproductive organs:

*Stamens.*—Number: 25–35. Length (mm): 2–5. Color (Munsell color charts): 5Y 8/10.

*Pistils.*—Number & location: About 200–300 pistils attached on the surface of the receptacle. Length (mm): 1.8. Color (Munsell color charts): 2.5Y 8/12.

Fruit shape: Conic.

Fruit size & color:

*Development stage.*—Green fruit: At maximum size about 1–2 days before starting to turn to pink. Size: Length (mm): 30. Diameter (mm): 21. Color (Munsell color charts): Exterior: 2.5GY 8/6. Flesh: White (no color chart given). Pink fruit: About 1–2 days before red. Size: Length (mm): 40. Diameter (mm): 35. Color (Munsell color charts): Exterior: 7.5R 4/16. Flesh: 7.5R 4/14. Ripe fruit-red: About 1–2 days after pink. Size: Length (mm): 40–51. Diameter (mm): 35–45. Weight (gram/fruit): Average: 23.8. Primary: 30. Color (Munsell color charts): Exterior: 6.25R 3/12. Flesh: 7.5R 4/12. Red color either from middle to both ends or from tip to shoulder.

Peduncle:

*Of flowers.*—Flower at fully open stage. Length (mm): 14.2. Diameter (mm): 2.5. Color (Munsell color charts): 5GY 7/6.

*Of fruits.*—Red ripe fruit stage. Length (mm): 15.7. Diameter (mm): 3. Color (Munsell color charts): 5GY 6/8.

Pedicel:

*Of flowers.*—Flower at fully open stage. Length (mm): 4.7. Diameter (mm): 1. Color (Munsell color charts): 5GY 7/6.

*Of fruits.*—Red ripe fruit stage. Length (mm): 7.9. Diameter (mm): 2. Color (Munsell color charts): 5GY 6/8.

Seeds:

*Number* (*mean*)/*fruit.*—243.

*Shape.*—Oblong.

*Size.*—length (mm): 1–1.5. diameter (mm): 0.5–1.

*Color* (*Munsell color charts*).—5YR 6/10.

Calyx position: Even/slight. Indent.

Seed position: Indent.

The yield of 'Treasure' is compared below with those of 'Camarosa' and 'Sweet Charlie' in Table 4.

TABLE 4

Data on yield and fruits obtained from the 1998–99 fruiting season in Plant City, Florida.

| | | 'Treasure' | 'Camarosa' | 'S. Charlie' |
|---|---|---|---|---|
| Yield (gram/plt) | December | 80 | 40 | 76 |
| | January | 132 | 97 | 145 |
| | February | 128 | 80 | 106 |
| | March | 413 | 303 | 296 |
| | April | 187 | 267 | 44 |
| | Dec–Mar | 753 | 519 | 624 |
| | Dec–Apr | 940 | 786 | 667 |
| Size (gram/fruit) | Average | 24 | 28 | 15 |
| | Primary | 30 | 29 | 24 |
| Firmness (Fruit Pressure Tester) (gram per 5 mm diameter plunger tip) (Higher value firmer fruit) | mean | 504 | 485 | 437 |
| | range | 310–550 | 350–550 | 283–525 |
| Sugar content (a.k.a. Soluble Solids) (degree Brix) | mean | 10.5 | 9.8 | 9.5 |
| Skin color (Munsell color charts) | | 6.25R 3/12 | 7.5R 3/12-6.25R 3/12 | 7.5R 4/14 |

Data shown in Table 4 were collected during the 1998–1999 fruiting season. The plants for the data came from meristem cultured plants produced in Florida, which were then increased in Canadian nurseries, and grown on three different farms in Plant City, Fla. during the 98/99 fruiting season.

Yield of 'Treasure' is higher than that of 'Camarosa' and 'Sweet Charlie'. The size of the primary fruit of 'Treasure' is similar to that of 'Camarosa', but larger than that of 'Sweet Charlie'. The firmness of the fruit is greater than that of 'Camarosa', and much greater than that of 'Sweet Charlie' as measured by Fruit Pressure Tester equipped with a 5 mm diameter plunger tip. The sugar content or sweetness, measured as soluble solids, of 'Treasure' is higher than those of 'Camarosa' and 'Sweet Charlie' as measured by Sugar/Brix Refractometer in degree Brix. The texture of the fruit is very firm. The skin color of the fruit is darker than those of Camarosa' and 'Sweet Charlie'. The finish is glossy and very attractive. The color of the flesh is similar to the skin but slightly less intense. The calyx is medium in size and positioned even or slightly indented to the base of the fruit. Seed placement is slightly indented to the fruit skin surface. The fruit is recommended for fresh market.

Because of its earliness, high yield, firmness, long shelf life and excellent fruit quality, this cultivar is considered to be competitive in the strawberry industry in Southeast United States.

We claim:

1. A new and distinct cultivar of strawberry plant named 'Treasure', as herein described and illustrated.

* * * * *